United States Patent [19]

Frost

[11] Patent Number: 5,057,322

[45] Date of Patent: * Oct. 15, 1991

[54] METHOD OF TREATING MAST CELL DISEASE

[75] Inventor: Phillip Frost, Miami Beach, Fla.

[73] Assignee: Baker Cummins Dermatologicals, Inc., Miami, Fla.

[ * ] Notice: The portion of the term of this patent subsequent to May 8, 2007 has been disclaimed.

[21] Appl. No.: 565,428

[22] Filed: Aug. 10, 1990

[51] Int. Cl.$^5$ .......................... A61K 9/28; A61K 9/60; A61K 9/48; A61K 31/44

[52] U.S. Cl. .................................... 424/474; 424/435; 424/449; 424/455; 424/456; 424/463; 514/282

[58] Field of Search ............... 424/451, 455, 456, 463, 424/474, 435, 449; 514/282

[56] References Cited

U.S. PATENT DOCUMENTS

| | | | |
|---|---|---|---|
| 4,454,142 | 6/1986 | Tuttle | 514/282 |
| 4,923,875 | 5/1990 | Frost | 514/282 |

*Primary Examiner*—Thurman K. Page
*Assistant Examiner*—Carlos Azpuru
*Attorney, Agent, or Firm*—Kirschstein, Ottinger, Israel & Schiffmiller

[57] ABSTRACT

A method of treating a patient suffering from mast cell disease comprising daily administration to such patient of from about 1 to about 150 mg of a pure narcotic antagonist, e.g., nalmefene or naltrexone. The antagonist may be administered in divided doses from one to four times daily, preferably by the oral route. Parenteral, transmucosal and transdermal administration may be utilized where suitable.

15 Claims, No Drawings

METHOD OF TREATING MAST CELL DISEASE

BACKGROUND OF THE INVENTION

1. Field of the Invention

The invention relates to methods of treating mast cell disease.

2. Description of the Prior Art

Mast cell disease is manifested in two, somewhat related conditions: urticaria pigmentosa and systemic mastocytosis.

Urticaria pigmentosa usually begins in early childhood and disappears partially or completely by adolescence. Characteristic skin lesions are single or multiple pigmented macules or nodules that urticate on rubbing and contain large numbers of mast cells.

Although uncommon, the disorder is seen in most dermatologic and pediatric practices. Light-skinned persons are affected most often, and it is slightly more common in males. The disorder has been reported in a parent and child in several families and in both members of monozygotic twins. More than 10 percent of cases are present at birth; over half develop by six months; and the majority appear before puberty. Onset after puberty raises the question of systemic mastocytosis.

Conventional treatments for urticaria pigmentosa have been relatively ineffective. Antihistamines may attenuate some of the symptoms, but aspirin and codeine degranulate mast cells and may aggravate symptoms. Although the disease is generally benign, in rare instances patients have developed serious complications such as infected bullae, peptic ulcers and bleeding tendencies.

Systemic mastocytosis, a rare, recently recognized disease, is being reported with increasing frequency. It affects both males and females and usually begins in adult life. The cause is unknown. The clinical manifestations and course may resemble those of lymphoma or leukemia, and it seems likely that the disorder should be classified with the reticuloendothelioses.

Skin or mucous membrane lesions may resemble childhood urticaria pigmentosa, but significant differences that indicate systemic mastocytoses are (1) onset after puberty, (2) multiple, small, confluent macules with persistent telangiectasia, (3) papules and nodules resembling leukemia cutis, (4) chronic lichenified dermatitis, (5) generalized infiltration of skin with a "scotch-grain" appearance, (6) less pigmentation, (7) less tendency to redden and urticate on stroking, (8) extensive involvement of oral, nasal, or rectal mucosa, and (9) progressive cutaneous change.

Histamine release into the general circulation is less likely than in childhood urticaria pigmentosa, yet patients may have flushing, shocklike episodes, and increased histamine in the urine. Diarrhea is often a prominent feature, and peptic ulcer occasionally develops.

The prognosis varies with the form of the disorder. Disease confined to skin and bone is compatible with long life and little morbidity, but there is always the threat of extension of the morbid process. Extensive reticuloendothelial involvement results in death in a few months to several years. Patients die from pancytopenia, infection, hemorrhage, cachexia, gastroenteritis, perforated peptic ulcer, and leukemia.

Conventional therapy is palliative and symptomatic and includes transfusions, antimicrobials, antihistamines, adrenal steroids, corticotrophin, roentgen irradiation, and nitrogen mustard.

Nalmefene (6-methylene-6-desoxy-N-cyclopropylmethyl-14-hydroxydihydronormorphine) is a long-acting, orally available, potent narcotic antagonist with pure antagonist activity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia (U.S. Pat. No. 4,511,570), sudden infant death syndrome (U.S. Pat. No. 4,639,455), autoimmune diseases (U.S. Pat. No. 4,857,533), arthritic and inflammatory diseases (U.S. Pat. No. 4,863,928), interstitial cystitis (U.S. Pat. No. 4,877,791), allergic rhinitis (U.S. Pat. No. 4,880,813). In commonly owned U.S. Pat. No. 4,923,875, the present inventor disclosed the utility of topical nalmefene in treating urticaria, various eczemas, and other mast cell-mediated dermatological disorders, but not the use of oral nalmefene in systemic mast cell disease. In commonly owned, published PCT Application No. US86/02268, it was disclosed that nalmefene is useful for the treatment of antigen-induced allergic responses, including those where degranulation of mast cells may be a causative factor.

Naltrexone (N-cyclopropylmethyl-14-hydroxydihydromorphinone) is another orally available narcotic antagonist with pure antagonist activity. Naltrexone has additionally been disclosed as useful for inducing anorexia (U.S. Pat. Nos. 4,477,457; 4,478,840) and for treating shock (U.S. Pat Nos. 4,267,182; 4,434,168), as well as for certain of the conditions cited above where nalmefene has been found useful.

In U.S. Pat. Nos. 4,877,791 and 4,923,875 it is disclosed that pure narcotic antagonists such as nalmefene and naltrexone may suppress histamine release from mast cells found in the bladder walls and the skin.

There does not currently exist any modality of drug treatment for mast cell disease, particularly systemic mastocytosis, which is known to be safe and effective in a significant number of cases.

SUMMARY OF THE INVENTION

It is the object of the present invention to provide a method of treatment for mast cell disease which may achieve symptomatic relief, prevent recurrence of the symptomatic phase and induce remission. In keeping with this object and others which will become apparent hereinafter, the present invention resides in the daily administration to patients suffering from mast cell disease of from about 1 to about 150 milligrams of a pure narcotic antagonist, e.g., nalmefene or naltrexone. The oral route of administration is preferred for patient convenience, comfort and safety, but parenteral and other methods of administration may be utilized.

DETAILED DESCRIPTION OF THE INVENTION

The method of treatment of the present invention consists of the daily administration to patients suffering from mast cell disease of from about 1 to about 150 mg of a pure narcotic antagonist. As used herein, the term "pure narcotic antagonist" refers to substances which block or reverse the effects of exogenous or endogenous opioids or opiates while having no intrinsic narcotic agonist activity themselves.

The oral route of administration is preferred so that the patient can self-medicate safely and conveniently. A number of the pure narcotic antagonists, for example nalmefene and naltrexone, are highly effective and substantially bioavailable when administered orally. For purposes of the present invention, however, any of the pure narcotic antagonists may be administered parenterally or via other routes of administration as well (e.g., transmucosally), as long as adequate blood levels are achieved.

Any pure narcotic antagonist may be used in the method of the present invention, but not mixed agonist-antagonists. Such pure narcotic antagonists include, by way of example but not limitation, naloxone, nalmefene, naltrexone and diprenorphine. Preferred agents are those which are orally active and which have a long duration of action, in particular nalmefene and naltrexone.

In accordance with the present invention, the pure narcotic antagonist may be administered to patients suffering from mast cell disease in any conventional oral, parenteral, transmucosal, transdermal or other known dosage form. Oral dosage forms may include conventional tablets, capsules, caplets, pills, liquids (solutions, suspensions or elixirs) and the like, including generally from about 0.5 to about 75.0 mg of the antagonist per dosage unit together with suitable, pharmaceutically-acceptable excipients, binders, sweeteners, coloring agents and other conventional additives.

Parenteral dosage forms may include conventional injectable solutions of the pure narcotic antagonists, for example, isotonic saline solutions, together with pharmaceutically acceptable buffers and preservatives. The parenteral dosage forms generally contain from about 0.5 to about 75.0 mg of antagonist per dosage unit and may be injected by the subcutaneous, intramuscular or intravenous routes.

Suitable transmucosal and transdermal dosage forms may include known sublingual, buccal and intranasal vehicles, as well as patches and topical vehicles containing penetrants which enhance transdermal absorption of the active antagonist ingredients. Examples of such transmucosal and transdermal vehicles may be found throughout the pharmaceutical literature, including in Remington's Pharmaceutical Sciences, 17th edition (1985).

By one preferred method, the pure narcotic antagonist may be initially administered to patients suffering from mast cell disease in total daily doses of about 1.0–10.0 mg, for example for a one-week period, with gradual increments in daily dose of about 1–40 mg up to a maximum of 150 mg (50 mg. t.i.d. or 75 mg b.i.d.).

In general, the method of the present invention is not dependent on any particular vehicle for the active narcotic antagonist agents or any particular route of administration. Any known method for getting effective treatment amounts of a pure narcotic antagonist into the bloodstream of the patient may be utilized.

Although there may be no need to administer the pure narcotic antagonists more than once or twice daily to achieve the results envisioned by the present invention, equally divided doses administered up to four times daily may be utilized. There have been few reports of any significant adverse effects with antagonists such as nalmefene or naltrexone at the dosage levels proposed by the present invention.

The following example provides an illustration of the method of the present invention. This example is not intended to limit or restrict the scope of the invention in any way, and should not be construed as providing dosage forms, regimens or methods of administration which must be utilized exclusively to practice the invention.

EXAMPLE

A patient diagnosed as suffering from systemic mastocytosis is administered a 0.5 mg. tablet of nalmefene twice daily for 7 days, after which the dosage is increased on a weekly basis to 1.0 mg, 5.0 mg, 10.0 mg, 15.0 mg and 30.0 mg b.i.d., respectively. The patient may be maintained at a total daily dose of 60 mg until his symptoms are stabilized and remission of the disease process is observed.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

1. A method of treating a patient suffering from a mast cell disease comprising the daily administration to the patient of from about 1 to about 150 mg of a pure narcotic antagonist.

2. A method according to claim 1 wherein said antagonist is selected from the group consisting of naloxone, nalmefene, naltrexone and diprenorphine.

3. A method according to claim 1 wherein the antagonist is nalmefene or naltrexone.

4. A method according to claim 1 wherein the antagonist is administered to the patient orally.

5. A method according to claim 4 wherein the antagonist is administered to the patient in an oral dosage form comprising a tablet, capsule, caplet, pill or liquid containing from about 0.5 to about 75.0 mg of antagonist per unit.

6. A method according to claim 6 wherein the antagonist is administered to the patient parenterally.

7. A method according to claim 6 wherein the antagonist is administered to the patient by the subcutaneous, intramuscular or intravenous routes.

8. A method according to claim 1 wherein the antagonist is administered to the patient transmucosally or transdermally.

9. A method according to claim 1 wherein the antagonist is administered to the patient from one to four times daily.

10. A method according to claim 9 wherein the antagonist is administered to the patient from one to three times daily.

11. A method according to claim 10 wherein about 1 to about 10 mg of antagonist is administered to the patient daily for an initial period, after which the dosage amount is gradually increased to a maximum of 150 mg daily.

12. A method according to claim 10 wherein said antagonist is nalmefene.

13. A method according to claim 11 wherein about 1 mg of nalmefene is orally administered to the patient daily for an initial period of about seven days, after which the dosage is gradually increased on a weekly basis up to about 60 mg daily.

14. A method according to claim 1 wherein said disease is urticaris pigmentosa.

15. A method according to claim 1 wherein said disease is systemic mastocytosis.

* * * * *